United States Patent [19]

Blatt

[11] 4,232,664

[45] Nov. 11, 1980

[54] ARM ELEVATOR AND SLING

[76] Inventor: Gerald Blatt, Ste. 440, 2840 Long Beach Blvd., Long Beach, Calif. 90806

[21] Appl. No.: 2,755

[22] Filed: Jan. 11, 1979

[51] Int. Cl.³ .............................................. A61F 5/40
[52] U.S. Cl. ................................................... 128/94
[58] Field of Search ............. 128/94, 83, 82, DIG. 15

[56] References Cited

U.S. PATENT DOCUMENTS

| 980,464 | 1/1911 | Wermuth | 128/94 |
|---|---|---|---|
| 1,304,153 | 5/1919 | Bugge | 128/94 |
| 2,594,809 | 4/1952 | Sanders | 128/94 |

OTHER PUBLICATIONS

Zimmer Catalog, p. C43, received 1974, "Arm Elevator".

*Primary Examiner*—John D. Yasko
*Attorney, Agent, or Firm*—Roylance, Abrams, Berdo & Farley

[57] ABSTRACT

A device for supporting an injured arm in any of several positions including a horizontal, sling position, a diagonal sling position and a vertical, elevated position. The device comprises a flexible, L-shaped envelope, a shoulder strap, a rear support assembly for releasably coupling the strap to the rear of the envelope, and a forward support assembly for releasably coupling the strap to the envelope in a plurality of variable positions. The strap has looped-fabric and looped-fabric engaging hooks thereon to adjust the strap's length. The envelope has looped-fabric on the outside and the forward support assembly has looped-fabric engaging hooks thereon so as to engage the envelope at any desired position.

16 Claims, 6 Drawing Figures

ARM ELEVATOR AND SLING

BACKGROUND OF THE INVENTION

The present invention relates to a device for supporting an injured arm in a variety of positions from a horizontal, sling position to a vertical, elevated position.

There is a need by a patient with an injured hand, arm, or shoulder, especially by the hand surgery patient, for a single support that will function properly in the normal arm sling position, the Velpeau position, and also in the elevated arm position. The normal arm sling position, in which the lower arm is substantially horizontal to the ground and the upper portion of the arm is substantially vertical to the ground, is required to provide support and limited protection to the hand, arm or shoulder during various daily activities. The Velpeau position, in which the lower portion of the arm extends diagonally across the chest of the patient and the upper portion of the arm extends at an acute angle towards the center of the body, is often used in clavicle fractures and is required to help control edema which follows surgery or specific injury to the hand or lower arm.

The elevated position is one in which the hand of the supported arm is even with the head or above the level of the head; and the body of the patient is usually in either a sitting or reclining position. The forearm in the elevated position is substantially vertical. The elevated position also differs from the sling positions in that the arm is supported from a mechanical support member separate from the patient's body.

Often these types of patients are victims of a crippling disease in both hands and have limited or very little use of the hand not in the sling. Therefore, it is critical that the support can easily be changed from the sling mode to the elevated mode and vice-versa by a hand with very limited dexterity.

Although various slings have been known in the prior art, they are all subject to numerous disadvantages. Thus, some prior art slings comprise a flexible envelope with a shoulder strap attached thereto. Usually, one end of the strap is adjustable so that the length of the strap can be modified to suit the patient. However, such slings are generally designed for and usable for a specific one of the positions needed for arm support. Thus, one form of sling can be used for horizontal or diagonal sling support and a completely different article, differently constructed, is used for vertical elevated support. Thus, if one patient requires support of two different types under different circumstances, at successive stages of recovery, or at different times of the day, more than one type of sling or arm elevator is generally necessary.

Moreover, while straps on the prior art slings have been variable in length, they have usually included a buckle which is very hard to manipulate, especially if the patient's other hand or arm is somewhat injured or of limited dexterity.

In addition, many of the prior art slings require lifting of the strap over the head of the user in order to remove the sling, which can be very difficult and in fact painful to the patient using the sling. Finally, many of the prior art slings are made of cloth, which is unable to be easily modified in size and shape requiring large inventory of sizes to accommodate patients of various sizes and shapes.

Accordingly, it is a primary object of the present invention to provide an arm sling and elevator which can be used for supporting an injured arm of a patient which is simple to use and easily adjusted.

Another object is to provide an arm sling and elevator which can assume either of the sling or elevated positions without removal by the patient.

Another object is to provide an arm elevator and sling which has a strap which is easily adjustable in length.

Another object is to provide an arm elevator and sling which is easily adjustable in size, such as by simple cutting, so as to reduce the overall inventory necessary and to provide a device which will not unravel on a cut edge.

Another object is to provide an arm elevator and sling which has an easily removable strap so as to be able to remove the device with little pain or exertion.

The foregoing objects are attained by providing a combined arm elevator and sling comprising a substantially L-shaped, flexible envelope for receiving the lower portion of an arm; the envelope being closed along the bottom and open at the top; a shoulder strap for supporting the envelope; a first assembly for coupling the rear end of the strap to the envelope adjacent the rear end thereof; and a second assembly for coupling the forward end of the strap to the envelope in a variable position extending from the forward end thereof rearwards toward the rear end thereof.

At least a portion of the outer surface of the envelope has looped-fabric thereon and the second assembly for coupling the forward end of the strap to the envelope includes looped-fabric engaging hooks so that the strap can be releasably coupled to the envelope in a variable position. By merely moving the coupling location of the second assembly to the envelope, the patient can change from the horizontal sling position to the diagonal sling position. Since this coupling is located towards the front or forward end of the envelope, the arm is securely located in the envelope and the envelope and arm do not tend to rotate back into the horizontal sling position. When it is desired to place the arm in the elevated position, the strap is disengaged from the first assembly and is formed into a relatively large loop of adjustable size which can be hooked over a separate support mounted or standing near a chair, bed or the like. This is accomplished by attaching both ends of the strap to the second assembly or by looping the strap back upon itself. In the case of most patients, this conversion can be accomplished unassisted by the patient using the structure of the present invention.

The shoulder strap is formed with an outside surface of looped-fabric and has two portions at opposite ends of looped-fabric engaging hooks, which allows the length of the strap to be readily changed with one hand.

The envelope is preferably formed mainly of foamed material which can be cut to the desired shape and size to fit the patient, without requiring a large inventory supply. Similarly, the foamed material will not unravel at the cut edge.

Both of the forward and rear coupling assemblies of the strap to the envelope are easily released, since they include the looped-fabric and looped-fabric engaging hooks, so that it is not necessary to lift the strap of the device over the head of the patient to remove the device. Rather, these couplings, either of them, can be released and the device simply removed from the patient.

Other objects, advantages and salient features of the present invention will become apparent from the following detailed description, which, taken in conjunction with the annexed drawings, discloses a preferred embodiment of the present invention.

DRAWINGS

Referring now to the drawings which form a part of this original disclosure:

DETAILED DESCRIPTION OF THE INVENTION

Figure 1:
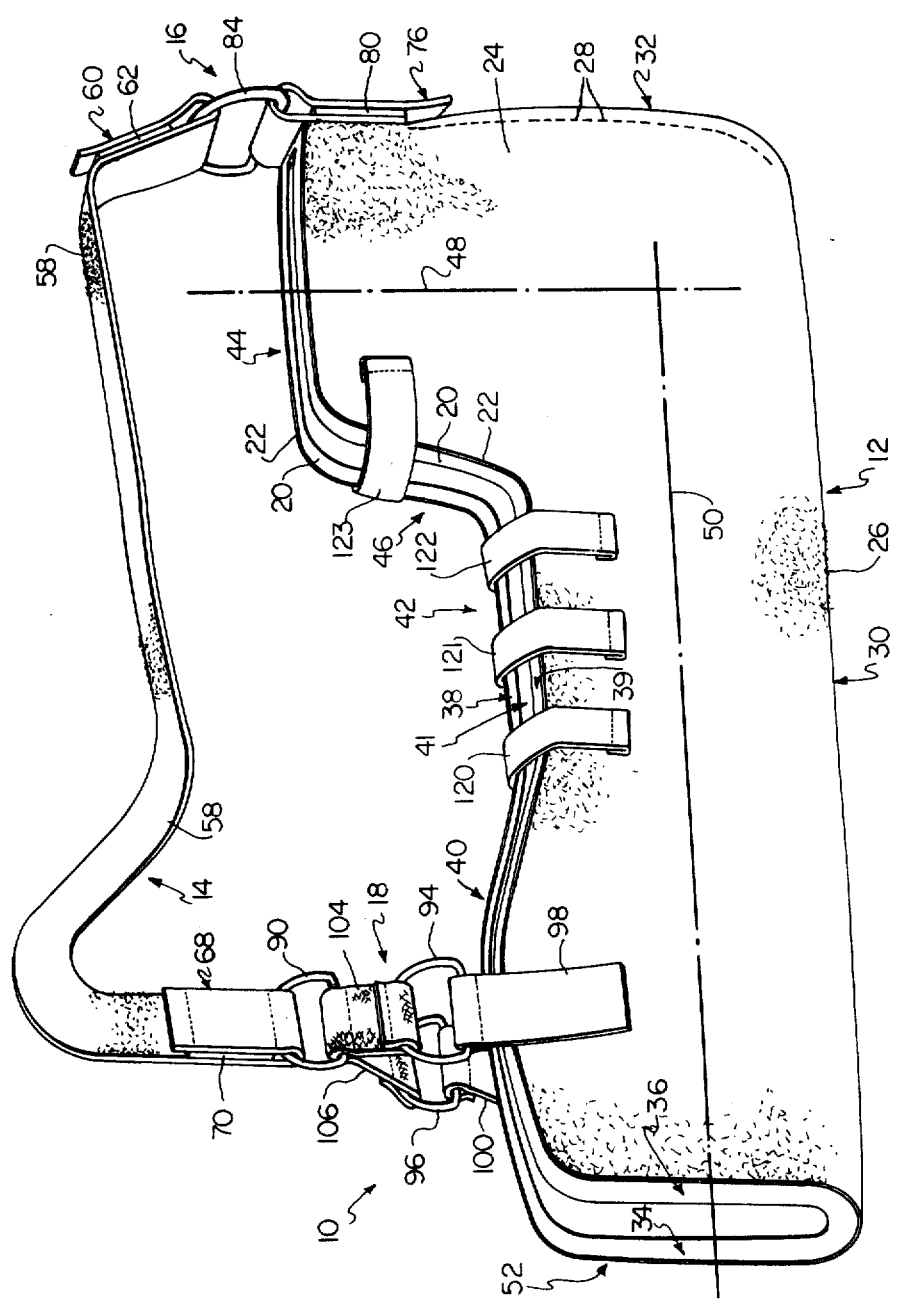
FIG. 1 is a perspective view in side elevation of the arm elevator and sling device in accordance with the present invention in the normal sling position.

As shown in FIG. 1, the arm elevator and sling 10 of the present invention comprises an envelope 12, a shoulder strap 14, a rear shoulder strap support assembly 16 and a forward shoulder strap support assembly 18.

The arm envelope 12 is L-shaped and is flexible, being formed from a laminate of a urethane foam layer 20 and a brushed nylon pile layer 22 with a surface of looped-fabric 24. This laminate is formed by an adhesive process or by a flame process. The material resulting therefrom is slightly stretchable and is capable of being cut without unraveling. As seen in FIG. 1, the urethane foam layer 20 is on the inside of the envelope 12 and the brushed nylon pile layer 22 is on the outside. As to be described in more detail hereinafter, the looped-fabric 24 forms the receiving or engaging portion of a releasable fastener such as that sold under the trademark VELCRO.

As seen in FIG. 1, the envelope 12 is formed with a longitudinal fold line 26 at the bottom edge and has the rear edges stitched together by stitching 28. The remaining edges of the envelope are open.

Accordingly, the envelope has a closed bottom edge 30, a closed rear edge 32, two forward, open edges 34 and 36, and two open top edges 38 and 39.

The top edges 38 and 39 of the envelope include a forward, convex portion 40, a flat mid-portion 42 and a flat rear portion 44, with a short vertical portion 46 extending between the mid-portion 42 and the rear portion 44.

When in use, the arm will be manipulated through the open top slot 41 between the top edges 38 and 39 with the elbow received in the area bound by the rear edge 32 and the bottom edge 30. The upper portion of the arm extends through the top slot at the rear portion 44 and in the sling position is oriented substantially along the phantom line 48. The lower portion of the arm assumes a position along phantom line 50 in the sling position and extends along the envelope to the forward end 52 adjacent the forward edges 34 and 36. The hand may extend past the forward edges if desired.

Figure 2:
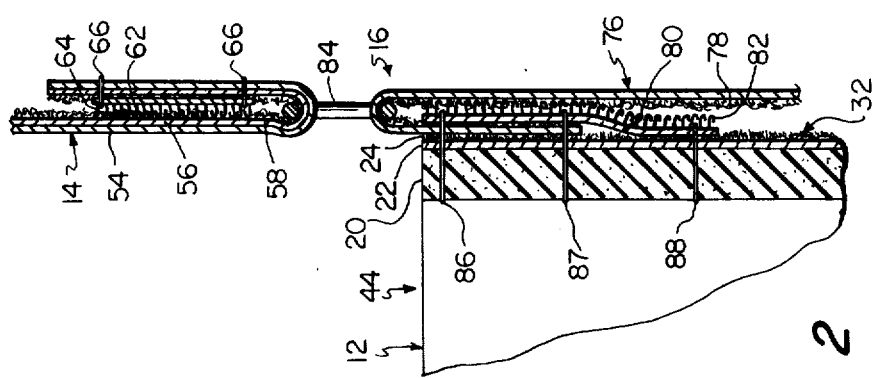
FIG. 2 is a fragmentary, longitudinal sectional view in side elevation of the rear shoulder strap support assembly shown in FIG. 1 specifically showing the releasable coupling of the rear end of the shoulder strap to the rear end of the envelope.
Figure 3:
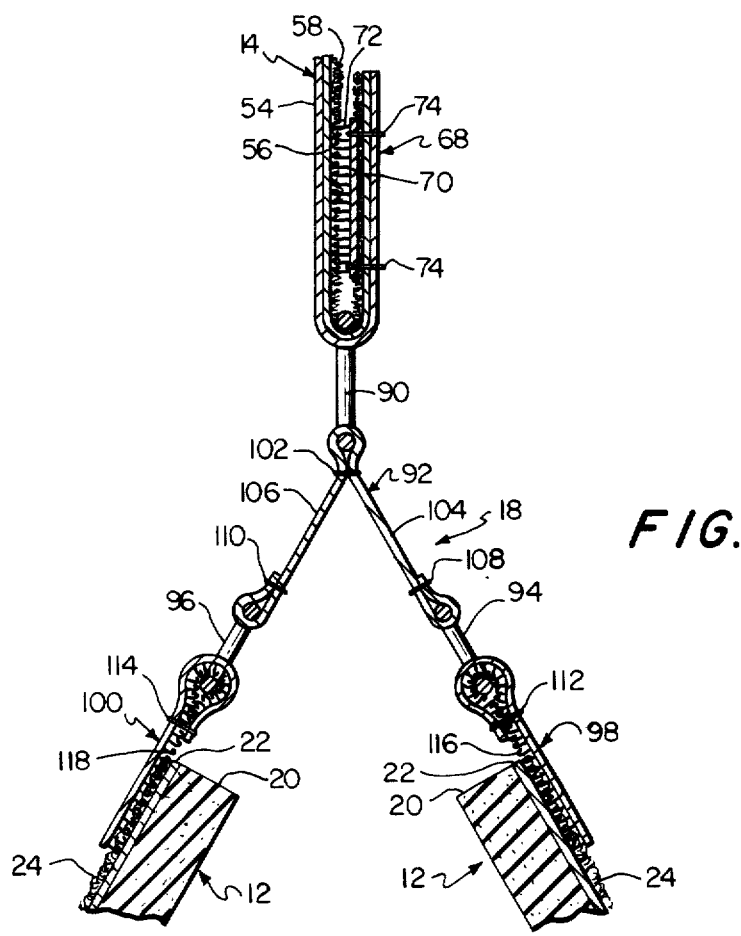
FIG. 3 is a fragmentary, transverse sectional view in front elevation showing the forward shoulder strap support assembly shown in FIG. 1 with its releasable coupling of the forward end of the shoulder strap to the forward end of the envelope.

Referring now to FIGS. 1, 2 and 3, the shoulder strap 14 is formed by a urethane foam layer 54 and a brushed nylon pile layer 56 adhered thereto, with the pile having a looped-fabric surface 58.

As seen in FIG. 2, at the rear end 60 of the shoulder strap 14 is a cloth support 62 having looped-fabric engaging hooks 64 extending therefrom, the cloth support 62 being stitched via stitching 66 to the end 60. These hooks 64 releasably engage the looped-fabric surface 58 on the shoulder strap itself forming a VELCRO type fastener.

Similarly, regarding FIG. 3, the forward end 68 of the shoulder strap 14 has a cloth support 70 with looped-fabric engaging hooks 72 extending therefrom, which cloth support 70 is stitched via stitching 74 to that end 68. These hooks 72 releasably engage the looped-fabric 58 of the shoulder strap 14 at the forward end thereof.

As seen in FIGS. 2 and 3, since one of the surfaces of the shoulder strap 14 is completely covered with looped-fabric 58, the hooks 64 and 72 at the opposite ends of the shoulder strap provide for adjustability of the length of the shoulder strap to almost any desired length.

Referring again to FIG. 2, the rear shoulder strap support assembly 16 comprises a support strap 76 having a looped-fabric surface 78, a cloth pad 80 having hooks 82 extending therefrom and a ring 84 receiving the support strap between the looped-fabric and the hooks. Both the cloth pad 80 and the support strap 76 are stitched via stitching 86 and 87 to the rear edge 32 of envelope 12 and the cloth pad 80 is similarly additionally stitched via stitching 88.

As seen in FIG. 2, ring 84 receives the rear end 60 of the shoulder strap 14, which passes therethrough, and the hooks 64 engage the looped-fabric 58 on the shoulder strap. Similarly, the support strap 76 extends through ring 84 and then releasably engages the hooks 82 on its looped-fabric 78. This rear shoulder strap support assembly therefore allows release of the shoulder strap from the rear of the envelope 12 merely by releasing the connection of hooks 82 and fabric 78. Thus, the arm elevator and sling 10 can be removed from the user without maneuvering the strap 14 over the head of the user.

Referring now to FIG. 3, the forward shoulder strap support assembly 18 is shown as comprising a ring 90, a cloth yoke 92, two rings 94 and 96 coupled to the cloth yoke and two short pads 98 and 100 respectively coupled to rings 94 and 96.

As seen in both FIGS. 1 and 3, cloth yoke 92 receives ring 90 therein at its midpoint and has stitching 102 below the loop receiving ring 90 to define a first leg 104 and a second leg 106. Leg 104 is looped at its distal end receiving therein ring 94 and securing the loop via stitching 108. Similarly, the second leg 106 passes through ring 96 and is folded back on itself and thereby looped, this loop being closed by stitching 110.

The short pad 98 passes through ring 94 and is folded back on itself forming a loop which is closed via stitching 112. The other short pad 100 passes through ring 96 and is folded back on itself to form a loop which is closed by stitching 114.

The short pad 98 has looped-fabric engaging hooks 116 extending from the surface thereof into releasable engagement with the looped-fabric 24 on the outside of envelope 12. Similarly, the other short pad 100 has looped-fabric engaging hooks 118 extending from a surface thereof into releasable engagment with the looped-fabric on the outside of the envelope 12.

As seen in FIG. 1, the entire outside surface of the envelope 12 is completely covered with looped-fabric 24 so that the hooks 116 and 118 on pads 98 and 100 of the forward shoulder straps support assembly 18 can be positioned on the outside of the envelope 12 variably as desired, such position extending from the forward end 52 thereof rearwards toward the rear end thereof. Similarly, by releasing the hooks 116 and 118 from looped-fabric 24, the forward shoulder strap assembly 18 can be completely removed from the envelope, thereby providing a simple manner of removing the device.

Figure 4:
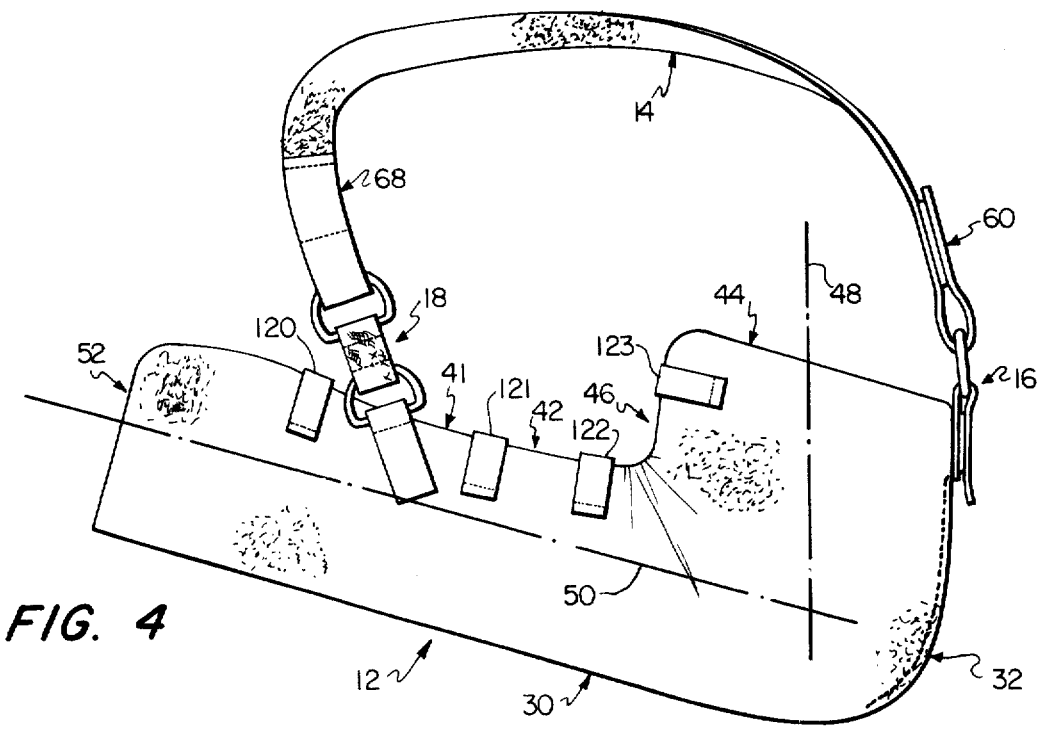
FIG. 4 is a side elevational view of the arm elevator and sling of the present invention in the diagonal sling position in which the shoulder strap has been shortened and the forward shoulder strap support assembly has been moved rearwardly along the length of the envelope.

Referring now to FIG. 4, the arm elevator and sling 10 is shown in the diagonal sling position in which the effective length of the shoulder strap 14 has been shortened by manipulation of either the forward end 68 or the rear end 60 of the strap and also the forward shoulder strap support assembly 18 has been moved rearwardly along the length of the envelope. As is evident, there is a slight flexing and creasing of the envelope 12 at the intersection of the vertical portion 46 and the midportion 42 of the top edges since the elbow of the arm has been manipulated to lessen the angle between the upper and lower arm portions of the person using the device. As seen in FIG. 4, the phantom line 48 representing the upper portion of the patient's arm is no longer perpendicular to phantom line 50 which represents the lower portion of the patient's arm. Rather, the upper arm phantom line 48 is offset at an acute angle from its previous vertical position shown in FIG. 1 and the lower arm phantom line 50 is no longer horizontal but instead it is diagonal as it extends across the chest of the wearer.

As seen in FIG. 1, a plurality of short straps 120, 122, 123 and 124 span the top edges of the envelope so as to aid in securing the arm inside the envelope. Each of these short straps has looped-fabric engaging hooks, not shown, extending from one surface, so that these straps can releasably couple themselves to the outer surface looped-fabric layer 24 on the envelope 12. As seen in FIG. 1, each end of the straps can have a small loop and stitching therein to provide a slight raised edge for easy removal of the straps. Comparing FIG. 1 and FIG. 4, it is seen that any one of the straps 120, 121, 122 or 123, can be moved to a different position along the top edges of the envelope 12 when the device is changed from its horizontal position shown in FIG. 1 to the diagonal sling position shown in FIG. 4. Specifically, in FIG. 4, the front short strap 120 is maneuvered to a position in front of the front shoulder strap support assembly 18 so that that assembly 18 can be in a releasable engaging relationship with the envelope 12 spaced a distance rearward of that shown in FIG. 1.

Figure 5:
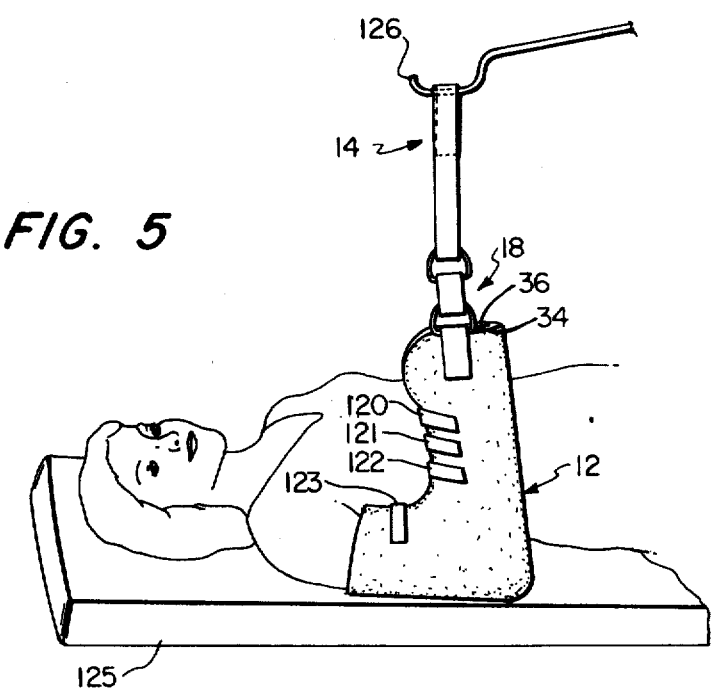
FIG. 5 is a simplified side elevation, in perspective, showing the device of the present invention in the elevated support position with the patient supine.
Figure 6:
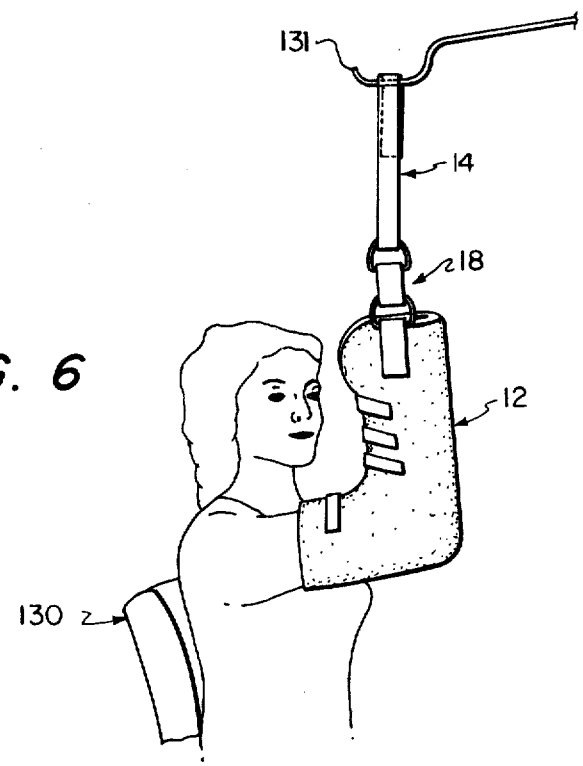
FIG. 6 is a simplified side elevation, in perspective, similar to FIG. 5 but with the patient seated.

Of particular importance is the use of the device of the present invention in the elevated position as shown in FIGS. 5 and 6, wherein the envelope 12 encases the patient's arm in the manner described with reference to FIG. 1. In FIG. 5, the patient is shown in the supine position on a bed, couch or the like 125. Strap 14 in this use of the device no longer serves as a shoulder strap. Instead, the rear portion 60 of the strap is disengaged from the rear support strap 76. Forward strap support assembly 18 is detached from the location occupied in FIG. 1 and is attached to the forward end of envelope 12 so that it extends across forward edges 34 and 36. The forward end 68 of strap 14 remains attached to ring 90. The rear end 60 of strap 14 is then formed into a relatively long loop so that it can be passed over an independently mounted bracket or hook 126 of conventional type. Hook 126 can be supported on a floor stand or a bracket attached to bed 125 in the usual fashion, the support therefor not being shown.

Strap 14 can be formed into the supporting loop in either of two basic ways, depending partly upon the height of hook 126 above the bed. The strap ends can be folded back on the strap as described, forming loops at both ends thereof somewhat in the way it is attached to itself as a shoulder strap as illustrated in FIG. 1. Alternatively, the ends of the strap can be attached to each other, forming one large loop. Because of the use of the hook and pile loop fasteners, the length in either case can be adjusted so that envelope 10 is supported in an appropriate and comfortable position with the tricep region of the upper arm supported by the inside of the rear edge 32 of the envelope and with edge 32 lightly resting on, or spaced above, the upper surface of bed 125.

As will be recognized, straps 120-123 perform a particularly important function in this vertical position because they permit the open top of the envelope to be closed in such a way that the forearm is completely enclosed and supported. These straps can, of course, be placed in any location for optimum support and comfort, and the number of straps can be selected as required by the anatomy and condition of the individual patient.

FIG. 6 is included to illustrate the use of the device of the invention with a patient seated in a chair 130, the arrangement and attachment of strap 14 between front assembly 18 and a support hook 131 being the same as that discussed with reference to FIG. 5. Hook 131 can, again, be part of a floor stand support or can be attached, for example, to the chair itself. In this arrangement, the length of strap 14 is usually adjusted so that the hand is at least as high as the patient's head, as prescribed by the attending physician.

While an advantageous embodiment has been chosen to illustrate the invention, it will be understood by those skilled in the art that various changes and modifications can be made therein without departing from the scope of the invention as defined in the appended claims.

What is claimed is:

1. An arm elevator and sling, comprising the combination of
   a substantially L-shaped, flexible envelope for receiving a portion of the arm of a patient including at least the elbow and the lower portion of the arm, said envelope being closed along the bottom and open at the top;
   shoulder strap means for supporting said envelope;
   first means for coupling the rear end of said strap means to said envelope adjacent the rear end thereof; and
   second means for coupling the forward end of said strap means to said envelope in a variable position extending from the forward end thereof rearwards toward the rear end thereof, said second means including
- a yoke assembly having two short pads, each of said pads having looped-fabric engaging hooks thereon,
- at least a portion of the outside surface of said envelope having looped-fabric thereon for releasably engaging said hooks.

2. The combination according to claim 1, wherein said yoke assembly comprises
- a ring receiving an end of said strap means, and
- means for coupling said ring to said two short pads.

3. An arm elevator and sling, comprising the combination of
- a substantially L-shaped, flexible envelope for receiving a portion of the arm of a patient including at least the elbow and the lower portion of the arm, said envelope being closed along the bottom and open at the top;
- shoulder strap means for supporting said envelope, having at the forward end at least a portion having looped-fabric thereon and at least another portion having looped-fabric engaging hooks thereon;
- first means for coupling the rear end of said strap means to said envelope adjacent the rear end thereof; and
- second means for coupling the forward end of said strap means to said envelope in a variable position extending from the forward end thereof rearwards toward the rear end thereof,
- said strap means passing through said second means and being folded back on itself so that said hooks engage said looped-fabric at any desired location thereon, thereby providing an adjustable length to said strap means.

4. An arm elevator and sling, comprising the combination of
- a substantially L-shaped, flexible envelope for receiving a portion of the arm of a patient including at least the elbow and the lower portion of the arm, said envelope being closed along the bottom and open at the top;
- shoulder strap means for supporting said envelope, said strap means having at the rear end at least a portion having looped-fabric thereon and at least another portion having looped-fabric engaging hooks thereon;
- first means for coupling the rear end of said strap means to said envelope adjacent the rear end thereof; and
- second means for coupling the forward end of said strap means to said envelope in a variable position extending from the forward end thereof rearwards toward the rear end thereof,
- said strap means passing through said first means and being folded back on itself so that said hooks engage said looped-fabric at any desired location thereon, thereby providing an adjustable length to said strap means.

5. An arm elevator and sling, comprising the combination of
- a substantially L-shaped, flexible envelope for receiving a portion of the arm of a patient including at least the elbow and the lower portion of the arm, said envelope being closed along the bottom and open at the top;
- shoulder strap means for supporting said envelope;
- first means for coupling the rear end of said strap means to said envelope in a variable position extending from the forward end thereof rearwards toward the rear end thereof
- said first means including
  - a support strap having looped-fabric thereon and coupled at one end to said envelope,
  - a pad containing looped-fabric engaging hooks thereon and located on said envelope to engage the looped-fabric on said support strap, and
  - a ring receiving said support strap between said looped-fabric and said hooks and also receiving the rear end of said strap means; and
- second means for coupling the forward end of said strap means to said envelope in a variable position extending from the forward end thereof rearwards toward the rear end thereof.

6. The combination according to claim 1, wherein said envelope has an outside surface completely covered by looped-fabric.

7. The combination according to claim 3, wherein said strap means has one surface completely covered by looped-fabric.

8. An arm elevator and sling assembly comprising the combination of
- a generally L-shaped envelope having a longer front leg portion for receiving the forearm of a patient and a shorter rear leg portion for receiving at least part of the upper arm of the patient adjacent the elbow, said envelope being generally U-shaped in transverse section with the top of the envelope being open and the bottom thereof being closed;
- strap means for supporting said envelope;
- first means coupled to the rear end of said envelope near the end of said rear leg for receiving an end of said strap; and
- second means selectively attachable to said envelope at a plurality of positions across the end of, and along the top of, said front leg portion, for receiving another end of said strap means;
- said assembly being usable as a sling by attaching said strap means between said first and second means with said second means bridging the open top of said envelope, and as an arm elevator by attaching said strap means between said second means and a separate support with said second means attached across the front end of said front leg portion.

9. The combination according to claim 8, wherein said second means comprises
- a yoke assembly having two short pads, each of said pads having a looped-fabric engaging hooks thereon,
- at least a portion of the outside surface of said envelope having looped-fabric thereon for releasably engaging said hooks.

10. The combination according to claim 9, wherein said yoke assembly comprises
- a ring receiving an end of said strap means, and
- means for coupling said ring to said two short pads.

11. The combination according to claim 8, wherein said strap means has at the forward end at least a portion having looped-fabric thereon and at least another portion having looped-fabric engaging hooks thereon,
- said strap means passing through said second means and being folded back on itself so that said hooks engage said looped-fabric at any desired location thereon, thereby providing an adjustable length to said strap means.

12. The combination according to claim 8, wherein said strap means has at the rear end at least a portion having looped-fabric thereon and at least another portion having looped-fabric engaging hooks thereon, said straps means passing through said first means and being folded back on itself so that said hooks engage said looped-fabric at any desired location thereon, thereby providing an adjustable length to said strap means.

13. The combination according to claim 8, wherein said first means comprises a support strap having looped-fabric thereon and coupled at one end to said envelope, a pad containing looped-fabric engaging hooks thereon and located on said envelope to engage the looped-fabric on said support strap, and a ring receiving said support strap between said looped-fabric and said hooks and also receiving the rear end of said strap means.

14. The combination according to claim 9, wherein said envelope has an outside surface completely covered by looped-fabric.

15. The combination according to claim 11, wherein said strap means has one surface completely covered by looped-fabric.

16. The combination according to claim 8, and further including a plurality of short straps having means for releasably coupling said short straps to the outside of said envelope so as to span the open top thereof.

* * * * *